United States Patent [19]

St. Angelo et al.

[11] Patent Number: 4,860,588
[45] Date of Patent: Aug. 29, 1989

[54] DEVICE FOR MEASURING WEATHERSTRIP TORSIONAL RIGIDITY

[75] Inventors: Stephen St. Angelo, Rochester Hills; John J. Lucci, Lansing, both of Mich.

[73] Assignee: General Motors Corporation, Detroit, Mich.

[21] Appl. No.: 255,262

[22] Filed: Oct. 11, 1988

[51] Int. Cl.$^4$ .............................................. G01N 3/26
[52] U.S. Cl. .................................. 73/794; 73/849
[58] Field of Search ............... 73/158, 794, 849, 854

[56] References Cited

U.S. PATENT DOCUMENTS 2,777,322  1/1957  Weber et al. .......................... 73/854
4,715,110  12/1987  St. Angelo et al. .................. 29/701

FOREIGN PATENT DOCUMENTS 838521  6/1981  U.S.S.R. ................................ 73/849

OTHER PUBLICATIONS

GM Engrg Standards, Vacuum Tubing (Non-Reinforced) pp. 105.201–105.204

Primary Examiner—Stewart J. Levy
Assistant Examiner—Michele Simons
Attorney, Agent, or Firm—Charles E. Leahy

[57] ABSTRACT

A measuring device measures the torsional rigidity of a motor vehicle weatherstrip of the type which tends to twist upon bending about its longitudinal axis as experienced during installation of the weatherstrip around a corner of a vehicle body opening. The measuring device includes a pair of a rotatably mounted arms carrying mounting shoes for gripping the weatherstrip at spaced apart points along the length of the weatherstrip. Pivot means mount the arms for movement to swing the mounting shoes in an arcuate path and thereby bend the weatherstrip about its longitudinal axis so that the weatherstrip tends to twist. An indicator clip is removably mounted on the weatherstrip intermediate the mounting shoes and twists with the twisting of the weatherstrip to indicate that the weatherstrip has experienced a predetermined degree of twisting during the arcuate bending of the weatherstrip. A readout gauge indicates the degree of bending which causes the weatherstrip to twist, thereby providing a measure of the torsional rigidity of the weatherstrip.

6 Claims, 3 Drawing Sheets

DEVICE FOR MEASURING WEATHERSTRIP TORSIONAL RIGIDITY

The invention relates to a measuring device and more particularly for measuring the torsional rigidity of channel shaped weatherstrips to be robotically installed upon a vehicle body.

BACKGROUND OF THE INVENTION

It is well known in vehicle bodies to install a weatherstrip around a door opening of the body so that closing the door against the weatherstrip seals the door opening against the entry of water. The weatherstrip conventionally includes a U-shaped cross-sectional portion with interior ribs which are adapted to engage over a sheet metal flange on the periphery of the vehicle body opening. A tubular elastomeric portion is interal with the U-shaped cross-sectional portion and projects outwardly of the door opening to be engaged by the door when the door is closed.

It is characteristic of such U-shaped cross-sectional weatherstrip that bending the weatherstrip around the corners of a door opening causes the weatherstrip to tend to twist. Such twisting may complicate the installation of the weatherstrip onto the flange of the door opening. The need for torsionally rigid weatherstrips is heightened by the advent of robotic installation of weatherstrips such as disclosed in U.S. Pat. No. 4,715,110, issued Dec. 29, 1987, Apparatus of a Robot for Installing Weather Stripping in a Door or Like Opening, Stephen St. Angelo et al, assigned to the assignee of this invention. Robotic installation of weatherstrips is facilitated if the weatherstrip is consistently capable of being bent by the robot tool without twisting.

Accordingly, it is desirable to provide a weatherstrip which is capable of bending without twisting. The tendency to twist is determined by the manufacturing variables such as the composition of the elastomeric material, the rigidity of a sheet metal or wire backbone incorporated into the U-shaped cross-section, and other manufacturing variables.

It would be desirable to provide a device for measuring the torsional rigidity of a weatherstrip, that is, the resistance of such a weatherstrip to twisting upon being bent. By testing weatherstrips for this resistance to twisting, weatherstrips could be consistently manufactured.

SUMMARY OF THE INVENTION

The present invention provides a device for measuring the torsional rigidity of a motor vehicle weatherstrip of the type which tends to twist upon bending about its longitudinal axis as experienced during installation of the weatherstrip on a flanged vehicle body opening. The measuring device includes a pair of a rotatably mounted arms carrying mounting shoes for gripping the weatherstrip at spaced apart points along the length of the weatherstrip. Pivot means mount the arms for movement to swing the mounting shoes in an arcuate path and thereby bend the weatherstrip about its longitudinal axis so that the weatherstrip tends to twist. An indicator clip is removably mounted on the weatherstrip intermediate the mounting shoes and twists with the twisting of the weatherstrip to indicate that the weatherstrip has experienced a predetermined degree of twisting during the arcuate bending of the weatherstrip. A readout gauge indicates the degree of bending which causes the weatherstrip to twist, thereby providing a measure of the torsional rigidity of the weatherstrip.

BRIEF DESCRIPTION OF THE DRAWINGS

These and other objects, features and advantages of the invention will become apparent upon consideration of the description of the preferred embodiment and the appended drawings in which.

DESCRIPTION OF THE PREFERRED EMBODIMENT

Figure 1:
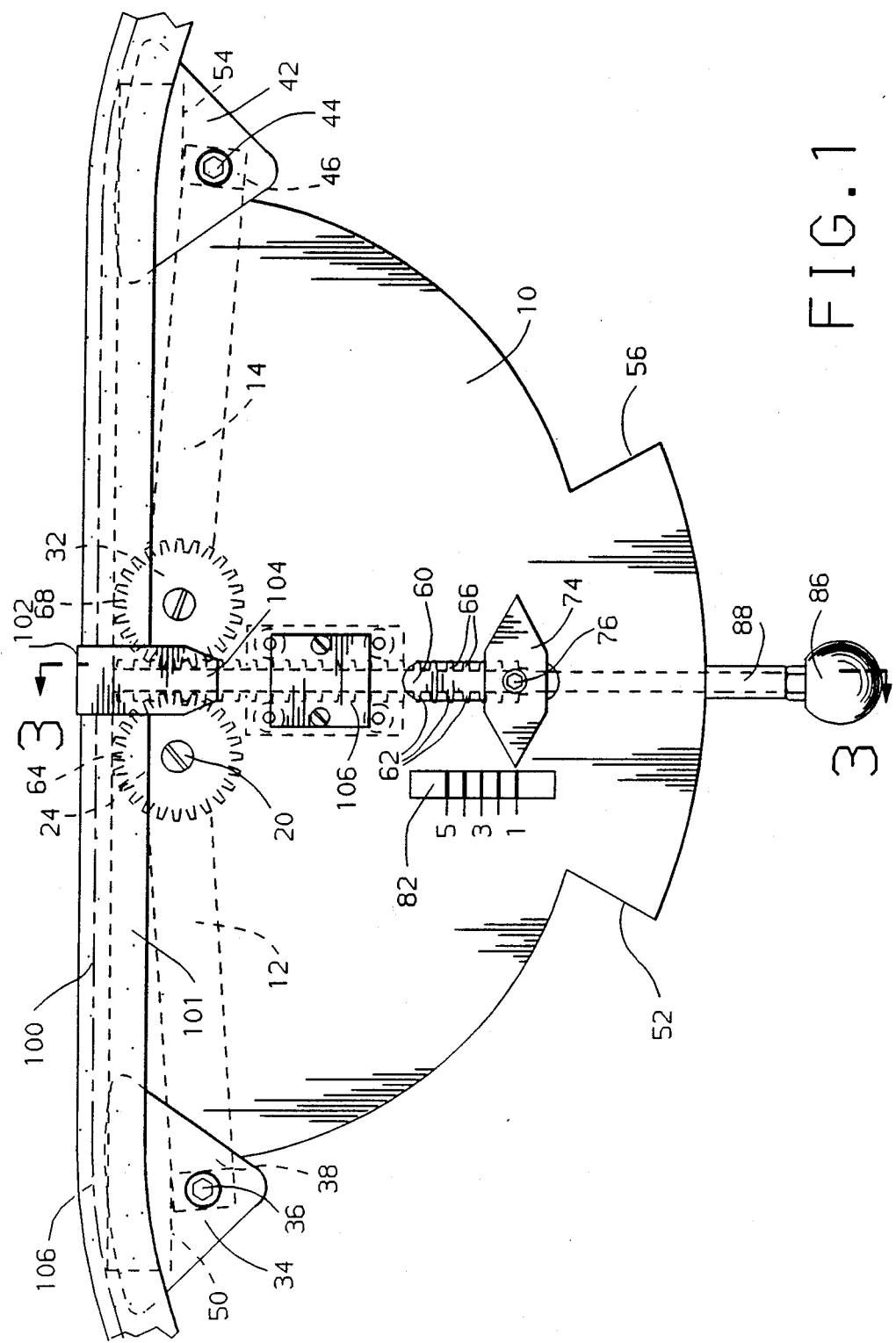
FIG. 1 is a front elevation view of the measuring device showing the weatherstrip gripped by the mounting shoes in readiness for testing.
Figure 2:
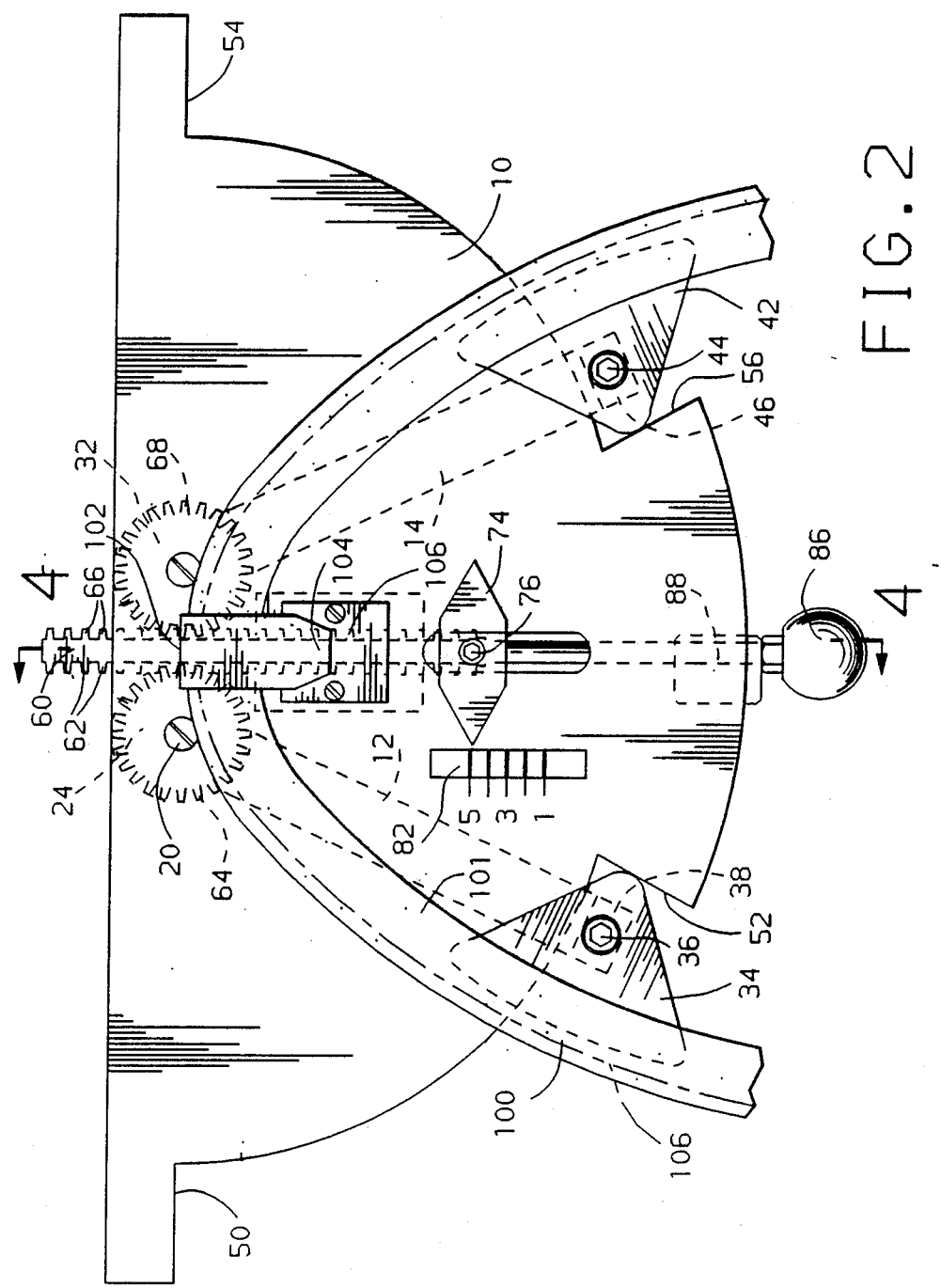
FIG. 2 is similar to FIG. 1 but showing the measuring device having been operated to bend the weatherstrip to such an extent that the strip has twisted and the readout indicator may be read to provide a measure of the torsional rigidity of the weatherstrip.
Figure 3:
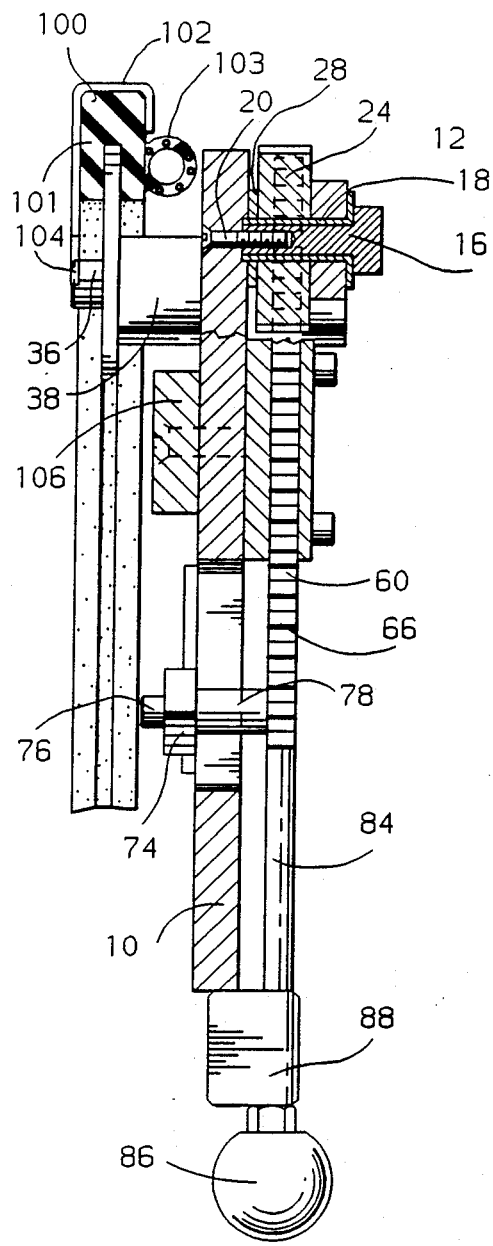
FIG. 3 is a sectional view through the measuring device taken in the direction of arrows 3—3 of FIG. 1.

Referring to FIGS. 1 and 2, it is seen that the measuring device of this invention includes a base plate 10 which may be mounted on a wall or on a standard, not shown, at a convenient working height to the test operator. A pair of pivot arms 12 and 14 are mounted on the base plate 10. As best seen in FIG. 3, the pivot arm 12 is mounted on the base plate 10 by a pivot shaft 16 which carries a bearing sleeve 18 and is attached to the base plate by a screw 20. The pivot arm 12 is fixedly attached to a pinion gear 24 which also rotates on the bushing 18. A thrust washer 28 is positioned between the pinion gear 24 and the base plate 10 to facilitate the low friction pivoting movement of the arm 12 and the pinion gear 24 about the pivot shaft 16. The pivot arm 14 is similarly mounted and has a pinion gear 32 associated therewith.

As best seen in FIGS. 1 and 3, a weatherstrip mounting shoe 34 is mounted on the end of the arm 12 by a bolt 36 and a extension bar 38 which is welded or otherwise suitably attached to the end of pivot arm 12. A similar mounting shoe 42 is mounted on the other pivot arm 14 by a screw 44 and an extension bar 46. As seen by comparing FIGS. 1 and 2, the pivot arm 12 may rotate about the pivot shaft 16 and thereby carry the mounting shoe 34 in an arcuate path between the position of FIG. 1 and FIG. 2. The FIG. 1 position of the pivot arm is established by the engagement of the extension bar 38 with a stop surface 50 of the base plate 10. The base plate 10 also has a stop surface 52 which is engaged by the extension bar 38 to limit the pivotal movement of the arm 12 at the other end of its arcuate travel. Similar stops 54, 56 are provided to limit the travel of the pivot arm 14.

As best seen in FIG. 1, the pinion gear 24 and 32 are spaced somewhat apart and a toothed rack 60 extends between the two gears. The toothed rack 60 has rack teeth 62 along the one side thereof which mesh with gear teeth 64 carried by the pinion gear 24. The toothed rack 60 also has teeth 66 on the other side thereof which mesh with gear teeth 68 of the pinion gear 32. Accordingly, comparing FIGS. 1 and 2, the coaction of the pinion gears 24 and 32 with the toothed rack 60 will serve to coordinate to a pivoting movement of the arms 12 and 14 and will cause the toothed rack 60 to move vertically up and down in direct proportion to the degree of pivotal movement of the arms 12 and 14. As best seen in FIGS. 1 and 2, a readout device is operated by the toothed rack 60 and includes a pointer 74 which is attached to the lower end of the toothed rack 60 by a screw 76 and an extension rod 78. The pointer 74 points to a scale 82 which is marked on the base plate 10.

A rod 84 extends downwardly from the bottom of the toothed rack 60 and carries a knob 86 and a lock 88. As best seen by comparing FIGS. 3 and 4, the lock 88 may be pivoted to a locking position of FIG. 3 in which the lock 88 acts between the base plate 10 and the knob 86 to prevent the upward movement of the toothed rack 60, and a pivoted position in FIG. 4 in which the locking block 88 is withdrawn from engagement with the base plate 10 to permit free up and down movement of the toothed rack 60.

Referring again to FIGS. 1 and 2, it is seen that the weatherstrip indicated at 100, having a U-shaped carrier 101 and tubular seal 103 is mounted on the mounting shoes 34 and 42 by simply snapping the weatherstrip over the mounting shoes in the same manner that the weatherstrip would be snapped over the flange of the vehicle body. As best seen in FIGS. 1 and 2, a pointer clip 102 is then snapped onto the weatherstrip 100 at a point midway between the mounting shoes 34 and 42. As best seen in FIG. 3, the mounting clip has a tip 104 which is spaced away from a block 106 which is mounted on the base plate 10.

Figure 4:
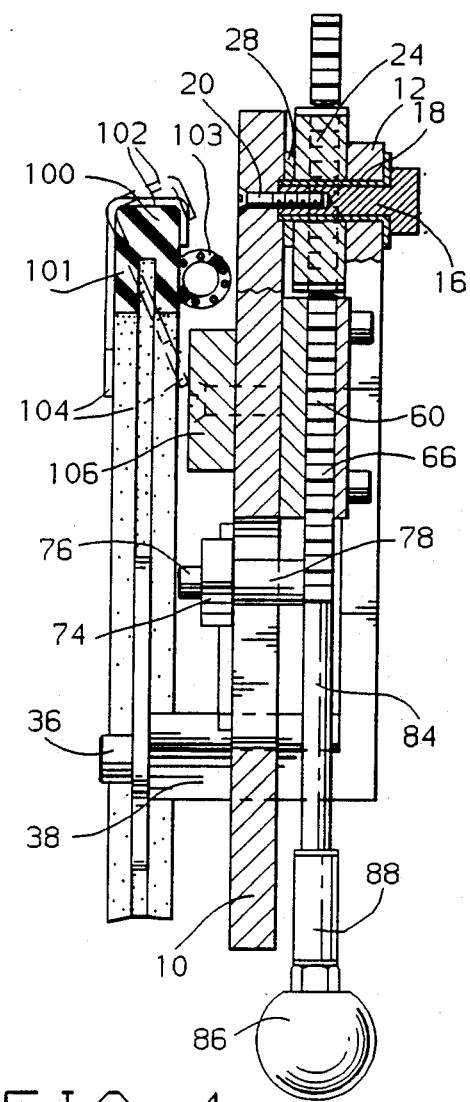
FIG. 4 is a sectional view through the measuring device taken in the direction of arrows 4—4 of FIG. 2.

The weatherstrip 100 is tested for torsional rigidity by the test operator griping the weatherstrip 100 and pushing downwardly on the ends of the weatherstrip to swing the arms 12 and 14 downwardly so that the mounting shoes 34 and 42 swing in an arcuate path and cause the weatherstrip 100 to bend about the longitudinal axis 106 thereof. As the weatherstrip 100 is progressively bent as shown in FIG. 2, the pointer clip 102 is moved downwardly with the weatherstrip as shown in FIGS. 2 and 4. When the weatherstrip twists, the pointer clip 102 twists with the weatherstrip and its tip 104 will eventually come into contact with the indicator block 106. The contact of the tip 104 with the mounting block 106 indicates that the weatherstrip 100 has experienced a predetermined degree of twisting. At this point, the operator reads the scale 82 to determine the amount of weatherstrip bending which has been achieved prior to the twisting of the weatherstrip. Accordingly, this gives a measure of the torsional rigidity of the weatherstrip, that is the resistance of the weatherstrip to twisting when the weatherstrip is bent.

Through experimentation, the degree of torsional rigidity necessary for optimum effectiveness of the weatherstrip installation robot may be determined. Then, using the measuring device, the manufacturing processing for manufacture of the weatherstrips may be controlled to provide torsional rigidity within the acceptable limits needed for effective robotic installation of the weatherstrip to the vehicle body.

The measuring device need not be used to measure every weatherstrip, but rather samples of weatherstrips can be tested.

Thus it is seen that the invention provides a device for measuring the torsional resistance of a weatherstrip to twisting upon bending of the weatherstrip about its longitudinal axis, particularly as may occur during the robotic installation of weatherstrips on a vehicle body.

The embodiments of the invention in which an exclusive property or privilege is claimed are defined as follows:

1. A device for measuring the torsional rigidity of a motor vehicle weatherstrip of the type which tends to twist upon bending about its longitudinal axis, comprising:
means gripping the weatherstrip at spaced apart points along the longitudinal axis of the weatherstrip and operable to bend the weatherstrip about its longitudinal axis so that the weatherstrip tends to twist;
indicator means indicating that the weatherstrip has experienced a predetermined degree of twist;
and read out means readable to identify the extent of bending of the weatherstrip causing the predetermined degree of twist to provide a measure of the torsional rigidity of the weatherstrip.

2. A device for measuring the torsional rigidity of a motor vehicle weatherstrip of the type which tends to twist upon bending about its longitudinal axis, comprising:
a base;
first and second arms having mounting shoes for gripping the weatherstrip at spaced apart points along the longitudinal axis of the weatherstrip;
pivot means pivotally mounting the arms for movement to swing the mounting shoes in an arcuate path to bend the weatherstrip about its longitudinal axis so that the weatherstrip tends to twist;
an indicator mounted upon the weatherstrip and indicating that the weatherstrip has experienced a predetermined degree of twist during the bending of the weatherstrip;
and read out means readable to identify the extent of bending of the weatherstrip causing the predetermined degree of twist to provide a measure of the torsional rigidity of the weatherstrip.

3. The device of claim 2 further characterized by gear means acting between the arms to coordinate the pivoting of the arms.

4. The device of claim 3 further characterized by rack means associated with the gear means acting between the arms to coordinate the pivoting of the arms and said rack means being operably associated with the read out means.

5. The device of claim 2 further characterized by the indicator mounted upon the weatherstrip being a pointer clip removably clipped onto the weatherstrip and twisting with the weatherstrip so that the degree of movement of the pointer clip indicates that the weatherstrip has experienced a predetermined degree of twist during the bending of the weatherstrip.

6. A device for measuring the torsional rigidity of a motor vehicle weatherstrip of the type which tends to twist upon bending about its longitudinal axis, comprising:
a base;
first and second arms having mounting shoes for gripping the weatherstrip at spaced apart points along the length of the weatherstrip;
pivot means pivotally mounting the arms for movement to swing the mounting shoes in an arcuate path to progressively bend the weatherstrip about length so that the weatherstrip tends to twist;
a pointer clip adapted to be removably clipped onto the weather strip intermediate the mounting shoes and twisting with the weatherstrip to provide and indication that the weatherstrip has experienced a predetermined degree of twist during the bending of the weatherstrip;

and first and second pinion gears attached respectively to the first and second arms and having teeth meshing with a toothed rack so that the pivoting of the arms is coordinated and the toothed rack moves in proportion to the arms and the arcuate swinging of the mounting shoes;

and a pointer attached to the toothed rack and having an associated scale which may be read to provide a quantitative measure of the torsion rigidity and resistance to twisting of the weatherstrip.

* * * * *